United States Patent [19]

Hales

[11] 4,278,651

[45] * Jul. 14, 1981

[54] SUPPORTED RECEPTOR AND USE THEREOF IN AN ASSAY

[75] Inventor: Richard H. Hales, West Jordan, Utah

[73] Assignee: Becton Dickinson & Company, Paramus, N.J.

[*] Notice: The portion of the term of this patent subsequent to Aug. 22, 1995, has been disclaimed.

[21] Appl. No.: 946,064

[22] Filed: Sep. 27, 1978

[51] Int. Cl.$^3$ .................. G01N 33/48; G01T 1/00
[52] U.S. Cl. ................................ 424/1; 23/230 B; 422/57; 422/59; 422/61; 424/12
[58] Field of Search ............... 424/1, 12; 23/230 B; 422/61, 57, 58, 59

[56] References Cited

U.S. PATENT DOCUMENTS

| | | | |
|---|---|---|---|
| 4,059,685 | 11/1977 | Johnson | 23/230 B |
| 4,108,975 | 8/1978 | Hales | 23/230 B |
| 4,166,102 | 8/1979 | Johnson | 424/1 |
| 4,217,338 | 8/1980 | Quash | 424/1 |

OTHER PUBLICATIONS

Am. Rev. Biochem. vol. 35, part II, pp. 875, 876, 878.

*Primary Examiner*—Benjamin R. Padgett
*Assistant Examiner*—Christine M. Nucker
*Attorney, Agent, or Firm*—Louis E. Marn; Elliot M. Olstein

[57] ABSTRACT

A supported receptor for use in an assay for a ligand in which the solid support includes a water insoluble polymer including at least one functional group which is either carboxyl, isothiocyanate, N-hydroxysuccinimide, imidazolide, bromoacetyl, maleimide, or diazomethylene, with the receptor being covalently linked to the support through the functional group. The preferred support is a particulate support including an impervious non-porous core and an outer porous coating having the water insoluble polymer, including the aforesaid functional groups, adhering thereto.

33 Claims, No Drawings

SUPPORTED RECEPTOR AND USE THEREOF IN AN ASSAY

This invention relates to the assay of ligands, and more particularly to a supported receptor for use in the assay of ligands.

In a solid phase competitive protein binding assay, for example, an antigen or hapten, can be assayed by a method which involves competition between an analyte and a labeled form thereof for a limited number of receptor or binder sites bound to a solid support. Thus, for example, when a known quantity of a labeled form of the hapten or antigen, a known quantity of a receptor for the antigen or hapten, and a sample containing the hapten or antigen are combined and incubated, the percentage of the labeled form of the antigen or hapten bound to the receptor will vary inversely with the quantity of antigen or hapten in the sample. After separating the receptor bound antigen or hapten from the antigen or hapten not bound to the receptor or remaining in solution, the amount of labeled component in either or both fractions may be compared with a standard curve to determine the quantity of antigen or hapten which was present in the sample.

In accordance with the present invention there is provided an improved solid supported receptor for use in such an assay.

In accordance with the present invention, there is provided a supported receptor for use in an assay for a ligand in which the solid support contains a water insoluble polymer including at least one functional group which is either carboxyl, isothiocyanate, N-hydroxysuccinimide, imidazolide, bromoacetyl, maleimide or diazomethylene, with the receptor being covalently linked to the support through the functional group.

In the case where the ligand to be assayed is an antigen or a hapten, the receptor which is covalently linked to the support may be an antibody, naturally occurring receptor or a serum protein. In the case where the ligand to be assayed is an antibody, the receptor which is covalently linked to the support is an antigen.

The solid support employed in the present invention may be the water insoluble polymer including such functional groups, by itself, or may be a suitable substrate having the water insoluble polymer, including the aforesaid functional groups, placed thereon.

In accordance with a preferred embodiment of the present invention, the water insoluble polymer is covalently linked to a particulate substrate which is resistant to dehydration and collapse. Such a preferred substrate is a material having a controlled surface porosity, superficially porous refractory particles made up of discrete macroparticles with impervious non-porous cores, and having joined thereto a coating of a series of sequentially adsorbed like mono-layers of like inorganic microparticles. The core is generally in the form of a sphere of a diameter of from 50 to 500 microns and composed of glass, although it may be of sand, ceramics and the like. The cores are preferably of uniform size; i.e., all within about 50 percent of the average diameter. Affixed to the core is a plurality of layers of microparticles which form an outer porous coating. The microparticles may range in size from 5 millimicrons to 1 micron, and the number of layers may be between 2 and 30. The microparticles may be amorphous silica, alumina, thoria and the like. Such a substrate has a relatively high surface area due to the porous coating, but is relatively free of pores in the core material. For beads of an overall diameter of 30 microns, and a porous crust of 1 micron, a surface area of between 0.8 to 1.0 $m^2/gm$ is obtained, with a packed bed density of 1.5 gms. per cc. The regular geometry, the stability against dehydration and collapse and the bulk renders the above material quite exceptional as a substrate. A typical such material is that available under the name "ZIPAX".

In accordance with such a preferred embodiment, the water insoluble polymer is adhered to the particulate substrate and this may be achieved in several ways.

Thus, for example, the water insoluble polymer may be adhered to the outer surface of the substrate by silane linkages. The substrate may be reacted with 3-aminopropyltriethoxysilane to form an aminoalkylsilane derivative in which the amino group is at the free end; i.e., a substrate-amine derivative. The amine derivative may then be treated with thiophosgene to convert the amino groups to isocyanate groups. Such isocyanate groups may then be reacted with a water insoluble polymer, such as dextran, cellulose, or a cellulose derivative such as carboxymethyl cellulose.

Alternatively, the particulate substrate may be reacted, for example, with vinyltrichlorosilane to provide a particulate support containing vinyl groups. A water insoluble polymer may then be adhered to the particulate support through such vinyl groups; e.g., by polymerization of a vinyl monomer, such as acrylonitrile, allylamine, acrylamide and the like.

The substrate having the water insoluble polymer adhered thereto may then be further treated, if necessary, to provide the functional group which is employed to covalently link a receptor thereto.

As representative examples of suitable water insoluble polymers which may be employed in accordance with the present invention, there may be mentioned: dextran, cellulose, carboxymethyl cellulose, polyacrylic acid, polyallylamine, polyallyl alcohol, polyacrylamide, polyallyl mercaptan, polyallyl cyanide, polyacrylonitrile, and the like.

The water insoluble polymer may be treated, if necessary, to provide the desired functional group. Thus, for example, the substrate after reaction with 3-aminopropyltriethoxysilane and thiophosgene to produce an isothiocyanate derivative may be reacted with cellulose or dextran to form a hydroxyl derivative which may in turn be treated with a halogenated acid such as bromoacetic acid, chloroacetic acid, 6-bromohexanoic acid or 5-chlorovaleric acid or succinic anhydride to form carboxyl functional groups for linkage to a receptor. Alternatively, the isothiocyanate derivative may be reacted with carboxymethyl cellulose to provide a polymer adhering to the substrate which includes carboxyl functional groups for linkage to a receptor.

In accordance with another embodiment, the substrate containing vinyl groups, prepared as hereinabove described, may be reacted with allylamine under polymerization conditions to form a polyallylamine coating linked to the particulate substrate. The polyallylamine may then be further treated to provide functional groups for covalent bonding to a receptor. Thus, for example, the polyamine derivative may be reacted with thiophosgene to provide polyisothiocyanate functional groups for linkage to a receptor.

Alternatively, the isothiocyanate functional groups may be reacted with carboxymethyl cellulose to provide carboxyl functional groups for linkage to a receptor.

As a further alternative, the isothiocyanate derivative may be reacted with dextran to produce a hydroxyl derivative which is then reacted with succinic anhydride or a halogenated acid, as hereinabove described to produce carboxyl functional groups for linkage to a receptor.

The allylamine derivative may be reacted with maleic anhydride, followed by reaction with a mixture of sodium acetate and acetic acid to produce maleimide functional groups for linkage to a receptor.

As a further alternative, the allylamine derivative may be reacted with urea to produce a urea derivative, which is then reacted with a mixture of sodium nitrite and sulfuric acid, followed by addition of potassium hydroxide to provide diazomethylene functional groups for linkage to a receptor.

As still another alternative the allylamine derivative may be reacted with o-bromoacetyl-N-hydroxysuccinimide to provide bromoacetyl functional groups for linkage to a receptor.

In accordance with a further embodiment, the substrate containing vinyl groups may be reacted with allyl cyanide under polymerization conditions to provide a polyallyl cyanide coating linked to the particulate substrate. The polyallyl cyanide may then be further treated with dextran or cellulose to provide hydroxyl groups, and the hydroxyl derivatives may be reacted with succinic anhydride or a halogenated acid to provide carboxyl functional groups for linkage to the receptor.

In accordance with still another embodiment, the substrate containing vinyl groups may be reacted with allyl mercaptan under polymerization conditions to provide a polyallyl mercaptan coating linked to the particulate substrate. The polyallyl mercaptan is then reacted with N,N'-o-phenylenedimaleimide to provide maleimide functional groups for linkage to a receptor.

In accordance with a still further embodiment, the substrate containing vinyl groups may be reacted with acrylamide under polymerization conditions to provide a polyacrylamide coating linked to the particulate substrate.

The polyacrylamide may then be converted to a polyimine (reaction with polyethyleneimine) or to a polyamine (reaction with a diamine such as ethylene diamine or hexamethylene diamine), followed by reaction with either succinic anhydride to provide carboxyl functional groups or o-bromoacetyl-N-hydroxysuccinimide to provide bromoacetyl functional groups.

In yet a further embodiment, the particulate support containing vinyl groups is reacted with acrylonitrile under polymerization conditions to provide a polyacrylonitrile coating linked to the particulate substrate. The polyacrylonitrile may be reacted with carboxymethyl cellulose to provide carboxyl functional groups. Alternatively, the polyacrylonitrile may be reacted with dextran or cellulose, followed by reaction with succinic anhydride or a halogenated carboxylic acid to provide carboxyl functional groups for linkage to a receptor.

As a further alternative, the polyacrylonitrile may be converted to a polyamide by reaction with Amberlite resin, which functional group can be converted to a polyester by reflux with absolute ethanol and hydrochloric acid. The polyester is converted to a polyhydrazide by reaction with hydrazine, which is then reacted with succinic anhydride to provide carboxyl functional groups for linkage to the receptor.

In still another embodiment, the particulate support containing vinyl groups is reacted with allyl alcohol under polymerization conditions to provide a polyallyl alcohol coating linked to the particulate substrate, which can then be reacted with succinic anhydride or a halo-substituted carboxylic acid to provide carboxyl functional groups.

In yet another embodiment, the particulate support containing vinyl groups is reacted with acrylic acid to provide a polyacrylic coating linked to the particulate support having carboxyl functional groups for linkage to a receptor. In the alternative, the carboxyl functional groups of the polyacrylic acid coating can be converted to N-hydroxysuccinimide functional groups by reaction with N-hydroxysuccinimide or can be converted to imidazolide functional groups by reaction with 1,1'-carbonyldiimidazole.

The above procedures and others for producing a polymer having the required functional groups should be apparent to those of ordinary skill in the art from the teachings herein.

The receptor is then linked to the support through the functional groups by reaction with either mercapto, carboxyl or amino groups of the receptor. Thus, for example, mercapto groups of the receptor can be linked through the maleimide functional group, and carboxyl groups of the receptor can be linked to the support through diazomethylene functional groups. The remaining functional groups employed in the present invention are employed to effect linkage to a receptor through an amino group of the receptor.

The receptor bound to a solid support in accordance with the present invention may be employed for the assay of any one of a wide variety of ligands. As representative examples of such ligands, there may be mentioned: polypeptides, nucleotides, nucleosides and proteins, such as ACTH, oxytocin, lutenizing hormone, insulin, proinsulin, Bence-Jones protein, chorionic gonadotropin, pituitary gonadotropin, growth hormone, renin, thyroxine binding globulin, bradykinin, angiotensin, follicle stimulating hormone; cyclic AMP; cholyl glycine, cyclic GMP, etc.; steroids, including: estrogens, gestrogens, androgens, adrenocortical hormones, bile acids, cardiotonic glycosides, aglycones as well as saponins. As specific examples, these may be mentioned: thyroxine, triiodothyronine, testosterone, androsterone, equilenin, estrone, estriol, progesterone, pregnenolone, 17-hydroxydeoxycorticosterone(compound S), deoxycorticosterone, cortisone, corticosterone, cortisol, aldosterone, digoxin, digitoxin, etc.; vitamins, such as vitamin A, folic acid, the B vitamin group, vitamin C, and D vitamins and vitamins E and K; and miscellaneous ligands, such as, antigens for Viral Hepatitis A and B, Rubella, Herpex Simplex, α-fetoprotein, etc.

The receptor bound to a solid support in accordance with the present invention is particularly suited for use in an assay which employs a flow through chamber, and in particular to an automated assay which includes regeneration of the receptor. Such an assay is described in U.S. Pat. No. 3,896,217 and U.S. Pat. No. 4,009,005, which are hereby incorporated by reference. As described in such patents, a sample containing a ligand to be assayed and a known concentration of a labeled form of the ligand is brought into contact with the supported receptor disposed in a chamber holder. When brought into contact, a portion of the mixture of labeled and unlabeled ligand binds to the receptor on the substrate.

Thereafter, the unbound ligand or the bound ligand or both are determined and concentration of the unlabeled ligand in the sample is determined from standard data. Thereafter, the receptor is eluted with an appropriate solution containing solvents such as methyl alcohol, isopropyl alcohol or ethyl alcohol or dimethyl formamide to effect a stoichiometric release of the bound labeled and unlabeled ligand from the receptor. The rinsing or eluting operation effectively regenerates the receptor for reuse, and thereafter, the same receptor may be used again, repeatedly, for assays of that ligand as to which the receptor is specific, with washings, as described between each use.

The invention will be further described with respect to the following examples; however, the scope of the invention is not to be limited thereby:

In the following examples, the antibody employed is progesterone antibody, except if otherwise indicated, however, other antibodies could be employed.

EXAMPLE I

A. Addition of Isothiocyanate Groups to Support

A 25 gm sample of Zipax is refluxed overnight (16 to 24 hrs.) with 40 ml (37.68 gm; 0.1702 moles) of 3-aminopropyltriethoxysilane in 400 ml of toluene. The Zipax is filtered, washed with toluene and then air dried for 30–60 min.

The 25 gm sample of Amine-Zipax is refluxed overnight (16–24 hrs) with 33.5 ml (50 gm; 0.435 moles) of thiophosgene in 300 ml of chloroform. The Zipax is again filtered, washed with chloroform and air dried for 30–60 min to produce a support containing isothiocyanate groups.

B. Preparation of Support Containing Vinyl Groups

A 25 gm sample of Zipax is refluxed for two hours with 41 ml (50.96 gm; 0.316 moles) of vinyltrichlorosilane in 85 ml of isooctane while being stirred mechanically. The Zipax is then filtered, washed with isooctane and acetone and either air dried or heated to 80° C. in an oven for two hours.

EXAMPLE II

The starting material is preparation IB.

A. A 6.25 gm sample of vinyl coated Zipax is refluxed for two hours in a mechanically stirred solution of 2.5 ml (2.66 gm; 0.0368 moles) of acrylic acid and 0.25 gm (1.032 mmoles) of benzoyl peroxide in 624 ml of acetonitrile. The polyacrylic acid coated Zipax is then filtered and Soxhlet extracted for one day each in acetonitrile, acetone and water, and then air dried.

B. A 300 mg sample of the Zipax-Polycarboxyl support is rotated for 45 min. at 4° C. in a conjugation tube containing 250 mg of 1-ethyl-3-(3-dimethylaminopropyl) carbodiimide dissolved in one ml of 0.1 M phosphate buffer, pH 5.0. After removal of the supernatant, one ml of a solution of antibody (progesterone antibody) salt precipitated from 0.1 ml of serum and previously incubated with cold antigen, dissolved in 0.1 M phosphate buffer, pH 5.0 is added and the mixture rotated at 4° C. for three days. The antibody-support is then filtered and washed with 0.5 M sodium bicarbonate solution, 0.1 M acetic acid-0.5 M NaCl solution (pH 4.0) and conjugation final buffer.

EXAMPLE III

A. Example IIA is repeated using 9.0 gm of vinyl coated Zipax, 6.34 ml of allylamine, 0.36 gm of benzoyl peroxide and 900 ml of acetonitrile.

B. A 5.10 gm sample of the Zipax-Polyamine support is refluxed overnight with 15 ml (22.62 gm; 0.197 moles) of thiophosgene in 100 ml of chloroform. After the reaction mixture is cooled, the support is filtered, washed with chloroform and air dried.

C. The salt precipitate from 0.1 ml of serum is dissolved in 0.8 ml of 0.1 M sodium bicarbonate solution and allowed to incubate with unlabeled antigen for 30 min. This mixture is added to 300 mg of support and rotated at 4° C. for three days. The antibody-support is then washed with 0.5 M sodium bicarbonate solution, 0.1 M acetic acid-0.5 M NaCl solution (pH 4.0) and conjugation final buffer.

EXAMPLE IV

A. The starting material is prepared as in IA.

The 25 gm sample of Isothiocyanate-Zipax is stirred for four hours in 400 ml of a 1% solution of dextran in water containing 2.69 gm (0.032 moles) of sodium bicarbonate. The pH of this solution is adjusted initially to 9.0 with 0.2 N NaOH. The Zipax is again filtered, washed with water and acetone, and air dried for 30–60 min.

B. A 1.23 gm sample of the polyhydroxyl coated Zipax (IVA) is heated to 53°–57° C. for 16–24 hours with 1.148 gm (11.47 mmoles) of succinic anhydride in 100 ml of dried, distilled pyridine. The mixture is cooled and the support filtered and washed with 100 ml each of 0.05 M HCl solution, 0.1 M HCl solution, water and acetone to produce polycarboxyl functional groups.

C. Antibody is linked to the support by the procedure of IIB.

EXAMPLE V

A. The starting material is IA.

A 5.03 gm sample of IA is stirred for four hours in 80 ml of a 1% aqueous carboxymethyl cellulose solution containing 0.67 gm (7.98 mmoles) of sodium bicarbonate. The pH of this solution is adjusted initially to 9.0 with 0.2 N NaOH. After the four hours the Zipax is filtered, washed with water and acetone and air dried and contains polycarboxyl groups.

B. Antibody is linked to the support as in IIB.

EXAMPLE VI

A. A support containing polyamine is prepared as described in IIIA.

B. Carboxyl functional groups are provided by the procedure described in IVB using the polyamine coated support instead of the polyhydroxyl coated support.

C. Antibody is linked to the support by the procedure of IIB.

EXAMPLE VII

A. Vinyl coated support (IB) is the starting material.

Procedure IIA is used with 15 gm of IB, 6.0 ml allyl alcohol, 0.60 gm of benzoyl peroxide and 1500 ml of acetonitrile. Mechanical stirring at room temperature for 16–24 hrs is used instead of reflux.

B. Carboxyl functional groups are provided by the procedure of IVB.

C. Antibody is linked to the support by the procedure of IIB.

EXAMPLE VIII

A. The starting material is IVA.

One gram of dextran coated Zipax is reacted with 14.703 gm (0.1058 moles) of bromoacetic acid in 19 ml of 40% NaOH solution with 20.641 gm (0.1058 moles) of 6-bromohexanoic acid in 19 ml of 40% NaOH solution, and with 5.0 gm (36.1 mmoles) of 5-chlorovaleric acid in 6.6 ml of 40% NaOH solution.

B. The support containing carboxyl functional groups is linked to antibody as described in IIB.

EXAMPLE IX

A. A 0.5 gm sample of acrylic acid modified Zipax, prepared as in IIA is stirred for 30 min. at room temperature with 1.158 gm (7.142 moles) of 1,1'-carbonyldiimidazole in 7.5 ml of tetrahydrofuran (THF). The support is then filtered, washed with THF and acetone, and then air dried.

B. Antibody is linked to support as in IIB.

EXAMPLE X

A. A 350 mg. sample of amine modified Zipax prepared as in IIIA above is stirred magnetically with 0.236 gm (1.0 mmole) of O-bromoacetyl-N-hydroxysuccinimide for 30 min. at room temperature in 8.0 ml of dioxane. The support is then filtered, washed with 0.1 M NaCl solution and acetone, and then air dried.

B. The reaction with antibody is conducted similarly to Step IIIC except that at the end of the three day reaction, the bicarbonate supernatant is removed, 10 ml of 0.2 M 2-aminoethanol (pH 8.5) is added, and the mixture is rotated for 24 hours at room temperature. This solution is then removed and the Zipax washed as before.

EXAMPLE XI

A. A one gram sample of amine modified Zipax, prepared as in IIIA above, is stirred overnight at room temperature with 0.70 gm (7.14 mmoles) of maleic anhydride in 25 ml of benzene. The support is then filtered and washed with benzene.

The washed support is then added to 10 ml of acetic acid containing 0.20 gm of sodium acetate and the mixture heated to 80° C. and stirred for six hours. After the reaction mixture has cooled, the support is filtered, washed with water and ethanol, and then air dried.

B. Antibody support linkage can be carried out in both acidic and basic reaction medium. The salt precipitate from 0.1 ml of serum is dissolved in 0.8 ml of either 0.1 M NaOAc buffer (pH 5.0) or 0.1 M phosphate buffer (pH 8.0). Each antibody solution is then added to and reacted for 20 min. at 30° C. with one ml of specially prepared Affigel-102 (6.2 $\mu$mole/ml) support as follows: Each one ml sample of Affigel is placed in a test tube and washed several times with dimethylformamide (DMF) using centrifugation for separation. Next, a solution of 150 mg of N-lipoyl succinimide in 2.0 mls of DMF is placed in each tube and several drops of 0.1 M NaHCO$_3$ are added. The contents of the tubes are mixed overnight at room temperature after which the excess of N-lipoyl succinimide is removed by centrifugation and the Affigel, which now contains lipoyl groups, is washed twice with DMF and twice with water. A ten ml volume of water containing 50 mg of sodium borohydride is next added to the Affigel and the sulfide bonds of the lipoyl groups reduced for 20 min. at 30° C. A few drops of acetone are added to reduce foaming. The excess NaBH$_4$ is removed by centrifugation and then the Affigel is washed twice with water. This is the support to which the acid and base solutions of antibody are added. At the end of the 30 minute period, the tubes are centrifuged and the acidic and basic supernatants (containing antibody with free thiol groups) are each removed and added to 300 mg of polymaleimide modified Zipax from XIA above. These mixtures are rotated for 20 min. at 30° C. after which the supernatant is removed and 10.0 ml of 0.1 M 2-mercaptoethylamine is added and the tubes rotated for 20 min. at 30° C. to deactivate any unreacted sites.

EXAMPLE XII

A. Procedure IIA is employed using 10.5 gm of vinyl coated Zipax, 4.44 gm (0.0625 mmoles) of acrylamide, 0.43 gm (1.78 mmoles) of benzoyl peroxide, and 1050 ml of acetonitrile. 5.0 gm of the polyacrylamide coated Zipax is suspended in five ml of water, 25 ml of 6 M hydrazine hydrate is added, and the mixture is stirred in a 50° C. water bath for seven hours. The support is then filtered and washed with 0.1 M NaCl solution until the filtrate is yellow when tested with 2,4,6-trinitrobenzenesulfonate.

B. A one gram sample of the polyhydrazide modified Zipax, prepared in XIIA is suspended in 30 ml of 0.1 M NaCl solution (by stirring) while 0.877 gm (8.8 mmoles) of succinic anhydride is added in portions over a 10.0 min. period. The pH is kept constant at 4.0 by addition of 2N NaOH. The reaction mixture is stirred at room temperature for an additional two hours and then the support is filtered, washed with 0.1 M NaCl and air dried.

C. Antibody is linked to the support by the procedure of IIB.

EXAMPLE XIII

A. A 5.1 gm sample of polyacrylamide coated Zipax, prepared as in XIIA is stirred mechanically for four hours at 80° C. in 75 ml of ethylene diamine. The mixture is then poured into 125 ml of ice water, filtered, and washed with 0.1 M NaCl solution until the washes are free of ethylene diamine as shown by the 2,4,6-trinitrobenzenesulfonate test.

B. Carboxyl groups are provided by the procedure of IVB using XIIIA as starting material and antibody linked thereto by the procedure of IIB.

EXAMPLE XIV

Example XIII is repeated, except that in XIIIA, 3.0 gm of acrylamide modified Zipax is suspended in 10 ml of water, to which is added 75 ml of a 30% polyethylene imine solution. The mixture is heated to 90° C. and reacted for six hours instead of four hours.

EXAMPLE XV

A. Procedure XA is carried out using the polyamine modified Zipax from XIIIA. The reaction is conducted in 10 ml of 0.1 M phosphate buffer, pH 7.5 instead of in dioxane. In the aqueous case, the 0-bromoacetyl-N-hydroxysuccinimide is not isolated.

B. Antibody is linked to the support as in XB.

EXAMPLE XVI

A. Procedure XA is repeated using polyimine modified Zipax produced in Example XIV.

B. Antibody is linked to the support by the procedure of XB.

EXAMPLE XVII

A. Procedure IIA is repeated using 1.0 gram of vinyl coated Zipax, 0.48 ml of allyl mercaptan and 0.6 grams of benzoyl peroxide in 300 ml of acetonitrile.

B. 1.0 gm of allyl mercaptan coated Zipax, prepared as in XVIIA is incubated at 30° C. for 20 min. in 10.0 ml of 0.1 M NaOAc buffer (pH 5.0) which has been saturated with N,N'-o-phenylenedimaleimide (about 0.75 mM). The support is then filtered, washed with water and dried.

C. Antibody is linked to the support in acid and base medium similarly to XIB described above using antibody containing free thiol groups obtained as described in XIB.

EXAMPLE XVIII

A. 5.0 gm of vinyl coated Zipax is refluxed with 2.97 ml (0.037 moles) of allyl cyanide and 0.25 gm (1.03 mmoles) of benzoyl peroxide in 625 mls of acetonitrile for two hours with mechanical stirring. The mixture is then cooled and the Zipax filtered, washed with acetonitrile, and Soxhlet extracted one day each with acetonitrile water and acetone.

B. 0.5 gm of the dried allyl cyanide modified Zipax is added to a suspension of 200 mg of dextran in 8.0 ml of boron trifluoride etherate which has been preheated to 85° C. The temperature is maintained at 85° C. and the mixture stirred magnetically for 72 hours at which time the support is cooled, filtered, washed with EtOH and acetone and then air dried.

C. Carboxyl groups are formed by the procedure of IVB and antibody linked thereto by the procedure of IIB.

EXAMPLE XIX

A. A 5.0 gm sample of vinyl coated Zipax is stirred mechanically at room temperature with 2.48 ml (2.00 mg; 37.67 mmoles) of acrylonitrile in 310 ml of acetonitrile while a solution of 0.25 gm (1.03 mmoles) of benzoyl peroxide in 315 ml of acetonitrile is rapidly added. The mixture is then refluxed for 2.0 hr. and then cooled and the Zipax filtered and Soxhlet extracted for one day each with acetonitrile and acetone.

B. A 1.5 gm sample of the acrylonitrile modified Zipax, prepared as in XIXA above is stirred mechanically at room temperature for four hours in 20 ml of a 1% carboxymethyl cellulose solution in 0.1 M NaHCO$_3$ (pH 9.0). The support is then washed with water and acetone and dried.

C. Antibody is linked to the support as in IIB.

EXAMPLE XX

A. A 1.5 gm portion of the acrylonitrile modified Zipax XIXA is placed with 10 gm of Amberlite RIA-400 C.P. ion exchange resin in 75 ml of water and refluxed for three hours while stirring magnetically. The resin is previously converted from the chloride form to the hydroxide form by removing the fines, placing the resin in a column and washing first with 1.5 liters of 2.8 N NaOH solution and then with water. After the end of the reaction time period, the mixture is cooled and the Zipax and Amberlite collected in a filter, washed with water and air dried. The Zipax is separated from the Amberlite by means of a 400 mesh wire screen to provide a Zipax-polyamide support.

The Zipax-Polyamide support (1.5 gm) is refluxed for five hours in 300 ml of absolute EtOH while HCl gas, generated by dripping concentrated hydrochloric acid into concentrated sulfuric acid, is bubbled through the reaction mixture. The addition of the gas is stopped and refluxing is continued for an additional 24 hours after which the support is filtered, washed with absolute EtOH and acetone, and then dried to produce Zipax-Polyester support.

1.0 gm sample of the Zipax-Polyester support is placed in a solution made up of 5.0 ml of 99% hydrazine hydrate, 5.0 ml H$_2$O and 0.5 ml EtOH and then refluxed for 20 hours. After the reaction mixture has cooled, the support is filtered, washed with water and acetone, and dried to produce hydrazine modified Zipax.

B. A 0.5 gm portion of hydrazine modified Zipax is suspended in 30 ml of a 0.1 M NaCl solution while 877 mg (8.8 mmoles) of succinic anhydride is added in portions over a ten minute period. The pH is then adjusted to 4.0 and maintained as such while stirring the mixture at room temperature for two hours. This support is then filtered, washed with 0.1 M NaCl solution, water and acetone, and then air dried.

C. Antibody is linked to the support by the procedure of IIB.

EXAMPLE XXI

A. A one gram sample of polyacrylic acid coated Zipax prepared as in IIA is rotated for 70 min. in a tube with 20 ml of dioxane containing 0.23 gm of N-hydroxysuccinimide (2 mmoles) and 0.38 gm of 1-ethyl-3-(3-dimethylaminopropyl) carbodiimide hydrochloride. The support is then filtered, washed with dioxane and methanol and dried.

B. Antibody is linked to the support by rotating 300 mg of the support from XXIA for 30 min. at 4° C. with 1.5 ml of a 0.1 M NaHCO$_3$ buffer solution (pH 8.7) containing the previously salt precipitated antibody. After removal of the supernatant the support is rotated at 4° C. for 1 hr. with a 1 M glycine-0.1 M NaOAc solution and then washed as in IIIC.

EXAMPLE XXII

A. Procedure IIA is repeated using 9.0 gm of vinyl coated Zipax, 6.34 ml (4.825 gm; 84.5 mmoles) of allylamine, 0.36 gm (1.49 mmoles) of benzoyl peroxide, and 900 ml of acetonitrile.

A 600 mg portion of the support coated with polyamine is refluxed for three hours in a solution of 500 mg (8.325 mmoles) of urea in 5 ml of water (pH 4.5). The reaction mixture is then cooled to 0° C. and 179 mg (2.753 mmoles) of NaNO$_2$ added. With slow mechanical stirring and while maintaining the temperature at 0° C., a mixture of 179 mg of conc. H$_2$SO$_4$ and 6 ml of H$_2$O is added. The reaction mixture is stirred for an additional hour and then the support is filtered, washed and dried. The dried support is then added to 10 ml of a 50% KOH solution and stirred for one hour at room temperature, filtered, washed with water and dried.

B. Antibody is linked to the support by procedure IIIC, except that 0.1 M phosphate buffer (pH 5.0) is used in place of 0.1 M NaHCO$_3$ buffer.

EXAMPLE XXIII

A. A three gram sample of polyacrylamide coated Zipax prepared as in XIIA is suspended in 10 ml of water and then added to 75 ml of hexamethylene diamine previously melted by heating to 90° C. The mixture is stirred mechanically for six hours at 80° C. and then cooled and mixed with a 0.1 M NaCl solution. Filtration of the support is followed by washing with 2 liters of the same 0.1 M NaCl solution and then drying.

A 236 mg (1.0 mmole) sample of O-bromoacetyl-N-hydroxysuccinimide prepared by the method of Santi and Cunnion (Biochem., 13, 481 (1974)) is stirred magnetically with 350 mg of the above support for 30 min. at room temperature in 8 ml of dioxane. The support is then filtered, washed with 0.1 M NaCl solution and acetone and then dried.

B. Antibody is conjugated to the support by procedure IIIC except that the reaction is run at room temperature instead of 4° C. and after the first supernatant is removed and before the support is washed with the regular washes it is reacted for 24 hrs. at room temperature with 10 ml of 0.2 M 2-aminoethanol (pH 8.5).

Numerous modifications and variations of the present invention are possible in light of the above teachings and, therefore, within the scope of the appended claims, the invention may be practised otherwise than as particularly described.

I claim:

1. A supported receptor for use in an assay for a ligand, comprising:
a solid support comprising a water insoluble polymer, said polymer including at least one functional group selected from the group consisting of N-hydroxysuccinimide, imidazolide, maleimide, and diazomethylene and a receptor for binding the ligand covalently linked to the support through said functional group.

2. The supported receptor of claim 1 wherein the functional group is N-hydroxysuccinimide.

3. The supported receptor of claim 1 wherein the functional group is imidazolide.

4. The supported receptor of claim 1 wherein the functional group is maleimide.

5. The supported receptor of claim 1 wherein the functional group is diazomethylene.

6. The supported receptor of claim 1 wherein the water insoluble polymer is selected from the group consisting of dextran, cellulose, carboxymethyl cellulose, polyacrylic acid, polyallylamine, polyallyl alcohol, polyacrylamide, polyallyl mercaptan, polyallyl cyanide, and polyacrylonitrile.

7. A supported receptor for use in an assay for a ligand, comprising:
a particulate support including an imprevious non-porous core, and an outer porous coating, said particulate support having a water insoluble polymer coating adhering thereto, said water insoluble polymer coating including at least one functional group selected from the group consisting of carboxyl, isothiocyanate, N-hydroxysuccinimide, imidazolide, bromoacetyl, maleimide and diazomethylene, and a receptor for binding the ligand being covalently linked to the support through said functional group.

8. The supported receptor of claim 7 wherein the water insoluble polymer is selected from the groups consisting of dextran, cellulose and carboxymethyl cellulose and the functional group is carboxyl.

9. The supported receptor of claim 7 wherein the water insoluble polymer is a polyallylamine which is derivatized to provide functional groups selected from the groups consisting of isothiocyanate, carboxyl, maleimide, diazomethylene and bromoacetyl.

10. The supported receptor of claim 7 wherein the water insoluble polymer is a polyallyl cyanide which is derivatized to provide carboxyl functional groups.

11. The supported receptor of claim 7 wherein the water insoluble polymer is a polyallyl mercaptan which is derivatized to provide maleimide functional groups.

12. The supported receptor of claim 7 wherein the water insoluble polymer is a polyacrylamide which is derivatized to provide functional groups selected from the group consisting of carboxyl and bromoacetyl.

13. The supported receptor of claim 7 wherein the water insoluble polymer is polyacrylonitrile which is derivatized to provide carboxyl functional groups.

14. The supported receptor of claim 7 wherein the water insoluble polymer is a polyallyl alcohol derivatized to provide carboxyl functional groups.

15. The supported receptor of claim 7 wherein the water insoluble polymer is a polyacrylic acid derivatized to provide carboxyl functional groups.

16. The supported receptor of claim 7 wherein the water insoluble polymer is a polyacrylic acid derivatized to provide functional groups selected from the group consisting of N-hydroxysuccinimide and imidazolide.

17. The supported receptor of claim 7 wherein the non-porous core is glass spheres and the outer porous coating is formed of microparticles.

18. The supported receptor of claim 17 wherein the water insoluble polymer is adhered to the support through vinyl groups.

19. The supported receptor of claim 17 wherein the water insoluble polymer is adhered to the support through silane linkages.

20. The supported receptor of claim 17 wherein the water insoluble polymer is selected from the group consisting of dextran, cellulose, carboxymethyl cellulose, polyacrylic acid, polyallylamine, polyallyl alcohol, polyacrylamide, polyallyl mercaptan, polyallyl cyanide, and polyacrylonitrile.

21. In an assay for a ligand employing a tracer and a receptor for binding the ligand, the improvement comprising:
employing as the receptor a supported receptor as defined in claim 7.

22. The assay of claim 21 wherein the assay includes regeneration of the receptor with an eluting solution to effect release of ligand and tracer from the receptor.

23. In a flow-through chamber for use in an assay for a ligand including a supported receptor for binding the ligand, the improvement comprising:
employing as the supported receptor a supported receptor as defined in claim 7.

24. The supported receptor of claim 1 wherein the water insoluble polymer is on a substrate.

25. In a flow through chamber for use in an assay for a ligand including a supported receptor for binding the ligand, the improvement comprising:
employing as the supported receptor a supported receptor as defined in claim 8.

26. In a flow through chamber for use in an assay for a ligand including a supported receptor for binding the ligand, the improvement comprising:
employing as the supported receptor a supported receptor as defined in claim 9.

27. In a flow through chamber for use in an assay for a ligand including a supported receptor for binding the ligand, the improvement comprising:
employing as the supported receptor a supported receptor as defined in claim 10.

28. In a flow through chamber for use in an assay for a ligand including a supported receptor for binding the ligand, the improvement comprising:
employing as the supported receptor a supported receptor as defined in claim 11.

29. In a flow through chamber for use in an assay for a ligand including a supported receptor for binding the ligand, the improvement comprising:
employing as the supported receptor a supported receptor as defined in claim 12.

30. In a flow through chamber for use in an assay for a ligand including a supported receptor for binding the ligand, the improvement comprising:
employing as the supported receptor a supported receptor as defined in claim 13.

31. In a flow through chamber for use in an assay for a ligand including a supported receptor for binding the ligand, the improvement comprising:
employing as the supported receptor a supported receptor as defined in claim 14.

32. In a flow through chamber for use in an assay for a ligand including a supported receptor for binding the ligand, the improvement comprising:
employing as the supported receptor a supported receptor as defined in claim 15.

33. In a flow through chamber for use in an assay for a ligand including a supported receptor for binding the ligand, the improvement comprising:
employing as the supported receptor a supported receptor as defined in claim 16.

* * * * *